United States Patent [19]

Atkinson et al.

[11] Patent Number: 5,141,501
[45] Date of Patent: Aug. 25, 1992

[54] SUCTION METERING AND MIXING DEVICE

[75] Inventors: Gordon E. Atkinson, Cedarville; James C. Bailey, Yellow Springs, both of Ohio

[73] Assignee: Vernay Laboratories, Inc., Yellow Springs, Ohio

[21] Appl. No.: 526,086

[22] Filed: May 21, 1990

[51] Int. Cl.⁵ .............................. A61M 31/00
[52] U.S. Cl. ..................... 604/269; 604/22; 604/19; 604/20
[58] Field of Search ............... 604/19-22, 604/4, 269

[56] References Cited

U.S. PATENT DOCUMENTS

| | | | |
|---|---|---|---|
| 3,807,401 | 4/1974 | Riggle et al. | 604/269 |
| 3,955,573 | 5/1976 | Hansen et al. | 604/269 X |
| 4,002,170 | 1/1977 | Hansen et al. | 604/269 |
| 4,447,191 | 5/1984 | Bilstad et al. | 417/12 |
| 4,516,398 | 5/1985 | Wuchinich | 604/35 X |
| 4,540,406 | 9/1985 | Miles | 604/269 |
| 4,547,186 | 10/1985 | Bartlett | 604/4 |
| 4,675,117 | 6/1987 | Neumann et al. | 210/789 |
| 4,744,785 | 5/1988 | Rosenthal et al. | 604/4 |
| 4,769,001 | 9/1988 | Prince | 604/4 |
| 4,775,360 | 10/1988 | Lane et al. | 604/4 |
| 4,834,890 | 5/1989 | Brown et al. | 210/739 |
| 4,838,855 | 6/1989 | Lynn | 604/49 |
| 4,846,800 | 7/1989 | Ouriel et al. | 604/4 |
| 4,863,590 | 9/1989 | Ohnishi et al. | 210/93 |

Primary Examiner—Mickey Yu
Assistant Examiner—Kerry Owens
Attorney, Agent, or Firm—Biebel & French

[57] ABSTRACT

A suction metering and mixing device is disclosed for collecting body fluids such as blood and simultaneously mixing an anticoagulant therewith. The device includes a suction passage having an inlet end and an opposite end for connection to a vacuum supply. A chamber is provided for controlling the flow of anticoagulant and includes an inlet port defining a passage for entry of anticoagulant into the chamber and a diaphragm dividing the chamber into first and second portions wherein the diaphragm is in contact with the inlet port to prevent flow of anticoagulant into the first chamber portion. A fluid connection is provided between the suction passage and the second chamber portion whereby a vacuum may be supplied to the second chamber portion from the suction passage and the diaphragm is drawn away from the inlet port to allow anticoagulant to flow into the first chamber portion. The anticoagulant then flows through a supply tube to a position adjacent to the inlet to the suction passage where it is mixed with blood entering the suction passage.

17 Claims, 3 Drawing Sheets

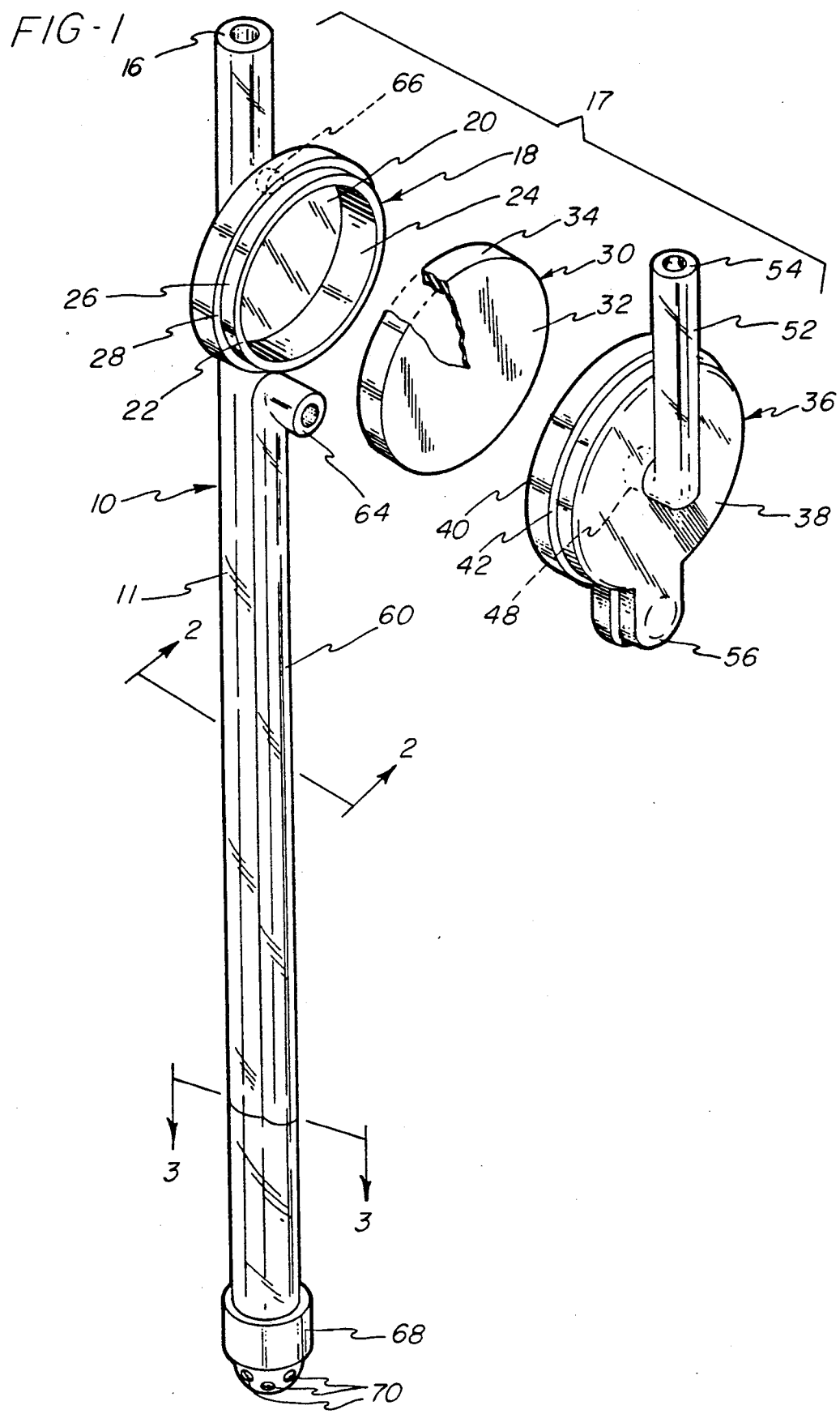

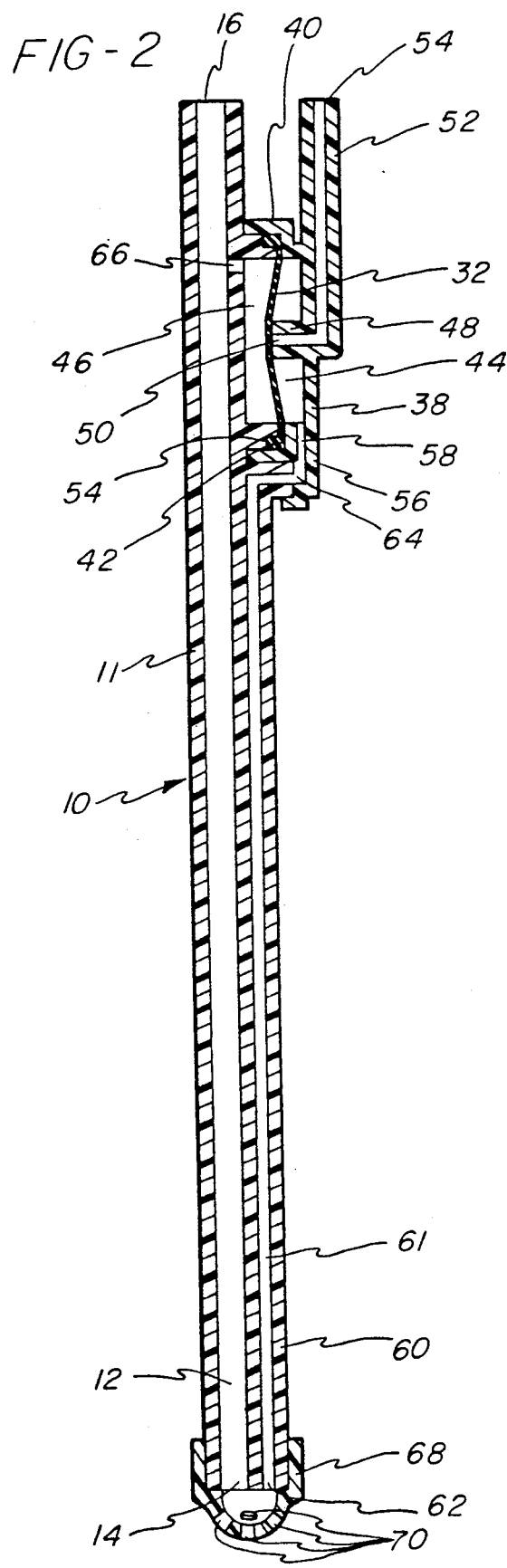
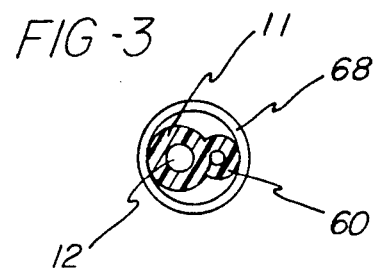

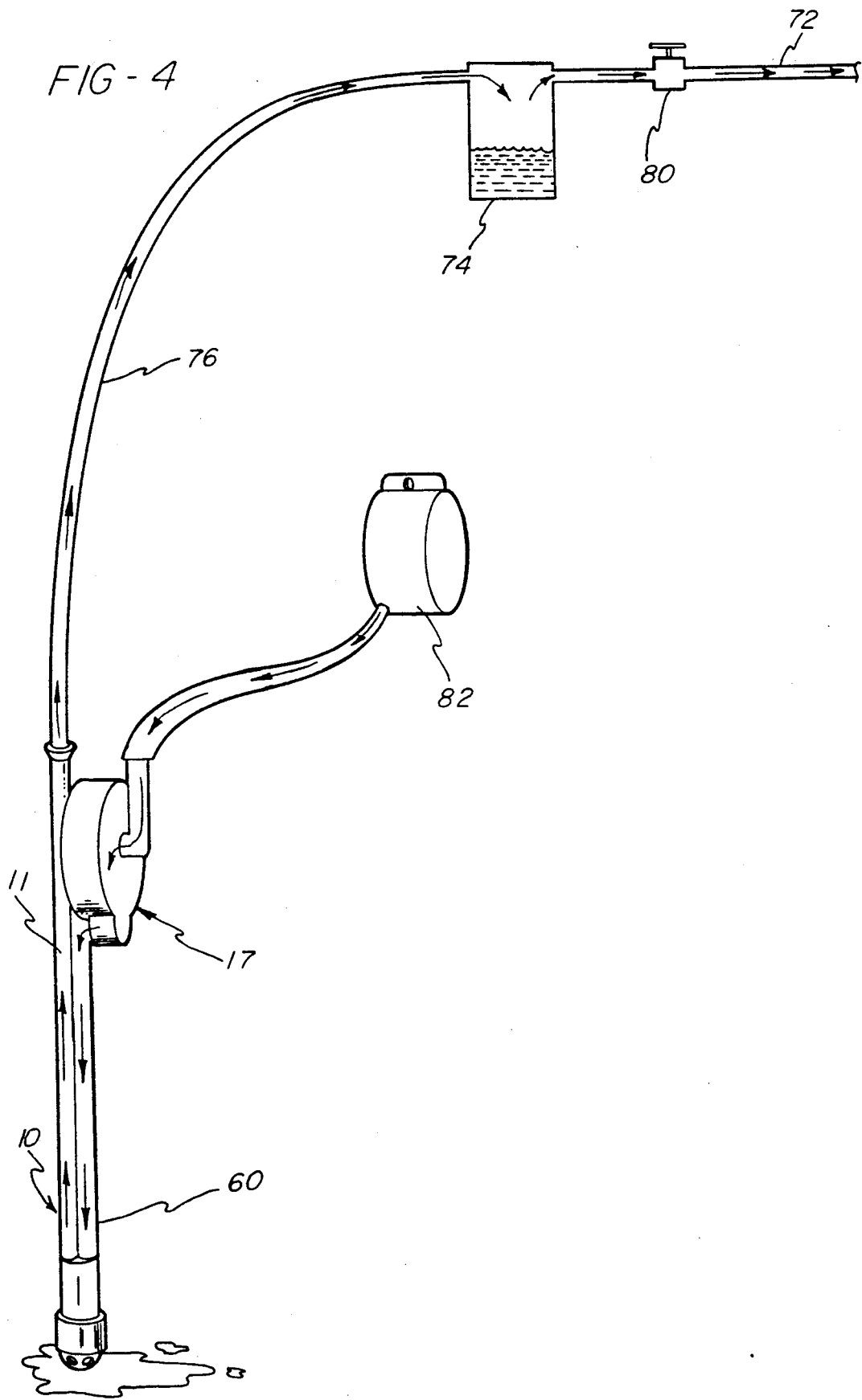

SUCTION METERING AND MIXING DEVICE

BACKGROUND OF THE INVENTION

The present invention relates to a suction device for aspirating blood during a surgical procedure and, more particularly, to a device for adding and mixing an anticoagulant with blood as it is sucked into the device.

During surgical procedures, especially those involving the abdominal or chest cavities, a great deal of bleeding occurs normally and conventional practice has been to simply aspirate the blood and other fluids to keep the surgical site clear and subsequently dispose of the fluids so removed.

A relatively recent development in this area has been to convey the blood and other fluids which are aspirated during surgery to a centrifuge, extract the red blood cells and serum and return the thus purified fractions to the patient during the surgical procedure. Since the blood begins to clot immediately upon contact with air, it is necessary to add an anticoagulant to the fluids aspirated, preferably as they are removed from the patient.

During this type of procedure, it is common to provide the operator with a on/off switch or clamp to terminate the suction and flow of the anticoagulant when the aspirator is not needed. Besides being somewhat awkward, it is not uncommon for the operator not to turn off the flow of anticoagulant, particularly in an emergency situation. As a result, an excess of anticoagulant may be added to the aspirated blood, thus increasing the rate of bleeding as the blood is returned to the patient.

U.S. Pat. No. 4,547,186 to Bartlett discloses a device for automatically introducing an anticoagulant into aspirated blood. In this device a bag of anticoagulant is provided for supplying anticoagulant at the point of aspiration as well as at a point along the blood flow line between the suction nozzle and the collection bag. However, the anticoagulant bag must be positioned at a particular height relative to the suction nozzle for the system to operate properly. Thus, it can be seen that this system requires a certain amount of calibration prior to use which may prove to be inconvenient in emergency situations.

Another system for metering anticoagulant during aspiration of blood is shown in U.S. Pat. No. 4,540,406 to Miles in which anticoagulant may be accurately metered to a suction nozzle regardless of the height difference between the nozzle and the anticoagulant supply. The suction nozzle of this device requires that the operator place his or her finger over an opening in the nozzle side in order to actuate the suction. While this device provides an improved amount of control over termination of the suction, the operator is required to give additional attention to accurate placement of his or her finger over the opening in the suction nozzle and as such introduces an increased amount of inconvenience into the aspiration procedure.

Accordingly, what is needed is a device for aspirating fluids from a patient during a surgical procedure which is capable of accurately metering anticoagulant for mixing with the aspirated fluids. In addition, the device must be capable of initiating and terminating flow of anticoagulant upon initiation and termination of the flow of fluids through the suction device such that a minimum of attention from the operator is required during use of the device.

SUMMARY OF THE INVENTION

The present invention is directed toward a suction metering and mixing device which may be used to remove fluids from the body cavity of a patient during surgical procedures.

The suction metering and mixing device of the present invention includes a suction passage for sucking a first fluid such as blood into the device. Means are also provided for supplying a second fluid such as anticoagulant to the suction passage as the first fluid is sucked into the device.

A chamber is provided for controlling the flow of the second fluid toward the suction passage whereby the flow of the second fluid is initiated in response to the presence of the first fluid within the suction passage, and is terminated in response to the absence of the first fluid within the suction passage. The chamber includes an inlet port defining a passage for entry of the second fluid which is conveyed from a container for supplying the second fluid.

A diaphragm divides the chamber into a first fluid supply portion and a second vacuum portion wherein the inlet port is in fluid communication with the first chamber portion. The diaphragm is normally located in a rest position in contact with the inlet port such that flow of the second fluid into the first chamber portion is prevented.

A fluid connection is provided between the second chamber portion and the suction passage intermediate a first end of the suction passage for receiving the first fluid and a second end of the suction passage which is adapted for connection to a vacuum source. When the first fluid is present within the suction passage, the vacuum source connected to the second end of the suction passage causes air to be drawn from the second chamber portion through the fluid connection such that a vacuum is supplied to the second chamber portion. The resulting sub-atmospheric pressure within the second chamber portion causes the diaphragm to be repositioned away from the inlet port of the first chamber portion to allow the second fluid to flow into the first chamber portion.

The first chamber portion is further provided with an outlet port such that the second fluid flowing into the first chamber portion is directed through the outlet port and into a tube which carries it to the first end of the suction passage. The second fluid is sucked into the suction passage with the first fluid whereby the first and second fluids are mixed together at the entry point to the suction metering and mixing device.

Thus, the present device provides accurate metering of the second fluid to be mixed with the first fluid such that the second fluid will only be supplied when the first fluid is present in the suction passage. In addition, when the device is no longer drawing the first fluid into the suction passage, the vacuum in the suction passage will be released as air is drawn into the passage and the diaphragm will return to its rest position in contact with the inlet port to terminate the flow of the second fluid.

Further, the present invention provides a device for aspirating fluids from a patient in which a minimum of attention is required for controlling the flow of anticoagulant to be mixed with aspirated fluids.

Other objects and advantages of the invention will be apparent from the following description, the accompanying drawings and the appended claims.

BRIEF DESCRIPTION OF THE DRAWINGS

FIG. 1 is an exploded perspective view of the suction metering and mixing device of the present invention;

FIG. 2 is a side view of the present invention shown in cross-section;

FIG. 3 is a cross-sectional view taken along line 3—3 in FIG. 1; and

FIG. 4 depicts the suction metering and mixing device of the present invention in combination with a blood collection and processing system.

DETAILED DESCRIPTION OF THE PREFERRED EMBODIMENT

Referring to FIGS. 1 and 2, the suction metering and mixing device of the present invention includes an elongated main body 10 including a suction tube 11 having a suction passage 12 formed therethrough. The suction passage 12 includes an inlet opening 14 at a first end of the suction tube 11 to define an inlet for receiving a mixture of blood and anticoagulant into the device and a second end 16 located at an opposite end of the suction tube 11 for connection to a vacuum source.

The main body 10 further includes a suction chamber 17 having a base portion 18. The base portion 18 includes a substantially circular base wall 20 which is preferably formed integrally with the suction tube 11 of the main body 10. A substantially circular chamber wall 22 extends from the base portion 20 in a direction away from the tubular main body 10 and defines an inner surface 24 and an outer surface 26 wherein a shoulder portion 28 is formed in the outer surface 26.

A diaphragm 30 having a substantially planar surface 32 and a flange portion 34 extending substantially perpendicularly from the outer edge of the planar surface 32 is positioned such that it extends across the suction chamber 17 with the flange portion 34 being seated on the shoulder portion 28 of the base portion 18. The diaphragm 30 is formed as a flexible element of the chamber 17 and is preferably formed of an elastomeric material.

The chamber 17 further includes a cap portion 36 having a substantially circular top portion 38 and a substantially circular cap wall 40 extending perpendicularly from the top portion 38 and connected to the top portion 38 by means of a shoulder portion 42. The cap 36 is positioned such that the cap wall 40 surrounds the chamber wall 22 and thereby holds the flange portion 34 of the diaphragm 30 in position against the wall 26. In addition, the shoulder portion 42 of the cap 36 engages the outer peripheral portion of the diaphragm 30 to thereby force the flange portion 34 into engagement with the shoulder portion 28 of the base portion 18 whereby the diaphragm 30 is held in position sandwiched between the base portion 18 and the cap 36.

It should be noted that the top portion 38 of the cap 36 is spaced from the shoulder portion 42 whereby a space is defined between the diaphragm surface 32 and the top portion 38 across the diameter of the chamber. Thus, it can be seen that the diaphragm 30 acts to divide the chamber into a first fluid supply portion 44 and a second vacuum portion 46.

The cap 36 is further provided with an inlet tube 48 extending from the top portion 38 a greater distance than the distance between the shoulder portion 42 and the top portion 38 such that an end 50 of the inlet tube 48 contacts the surface 32 of the diaphragm 30 and thereby slightly flexes the diaphragm 30 inwardly toward the base wall 20. The inlet tube 48 is preferably located centrally on the top portion 38 of the cap 36 and the end 50 forms an inlet port for passage of anticoagulant into the first chamber portion 44.

A feed tube 52 is connected to the inlet tube 48 and extends parallel to the suction tube 11. The feed tube 52 includes an inlet end 54 opposite from the inlet tube 48 whereby the feed tube 52 may be connected to a source of anticoagulant to supply anticoagulant to the first chamber portion 44.

The cap 36 is also formed with a tab portion 56 extending in a direction opposite from the feed tube 52. The tab portion 56 includes a supply passage 58 formed integrally therewith defining an outlet port for conveying anticoagulant from the first chamber portion 44. The supply passage 58 is connected to a supply tube 60 extending parallel to and having an interior fluid passage 61 of a lesser diameter than the suction passage 12. The supply tube 60 has a first outlet end 62 located adjacent to the first or inlet end 14 of the suction passage 12 and a second end 64 in fluid communication with the supply passage 58. Thus, the supply tube 60 will convey anticoagulant from the outlet port and supply passage 58 of the first chamber portion 44 to the outlet end 62 where it is in fluid communication with the first end 14 of the suction passage 12.

The second chamber portion 46 acts as a vacuum chamber and includes a fluid connection 66 to the suction passage 12 whereby a vacuum may be supplied to the chamber 46 from the suction passage 12. When a vacuum is supplied to the second chamber portion 46 such that a sub-atmospheric pressure is present within this portion of the chamber, the diaphragm 30 is drawn toward the base wall 20 to open the inlet port 50 and allow anticoagulant to flow into the supply tube 60 via the first chamber portion 44.

As may be seen in FIGS. 2 and 3, the main body portion 10 is formed with a circular cross-section near the outlet 62 of the tube 60 and the inlet 14 of the suction passage 12. A mixing cap 68 in the form of a half-sphere is positioned on the main body 10 over the openings 14, 62 to form a tip portion of the device. The mixing cap 68 includes a plurality of holes 70 through which blood may enter the device, and the cap 68 forms a mixing chamber for bringing anticoagulant into fluid communication with blood as it is being sucked into the suction passage 12.

As may be seen in FIG. 4, the suction metering and mixing device of the present invention may be connected to a suction source which is depicted as including a hospital vacuum line 72 supplying a vacuum to a blood collection and/or processing vessel 74, and a connecting vacuum tube 76 extending from the vessel 74 to the end 16 of the suction tube 11. In addition, an air metering means 80, such as an air metering valve or orifice, is positioned between the hospital vacuum source and the vessel 74. The metering means 80 acts to limit the amount of air drawn through the suction tube 11 when fluid is absent from within the passage 12. Thus, the velocity of air flowing through the suction tube 11 will be limited to a relatively low level such that any pressure drop developed in the second chamber 46 as a result of air flow through the suction tube 11 will not be sufficient to cause the diaphragm 30 to move out of engagement with the inlet port 50.

In operation, the vacuum tube 76 may be connected to the end 16 of the suction tube 11 and a source of anticoagulant 82 may be connected to the inlet end 54 of the drip tube 52 and elevated above the main body 10. The holes 70 in the cap 68 may then be temporarily blocked such that a vacuum will be applied to the second chamber portion 46 to move the diaphragm 30 away from the inlet port 50 and allow anticoagulant to fill the drip feed tube 52, the first chamber 44 and the supply tube 60 whereby the path for supplying anticoagulant is primed for use.

When the holes 70 are unobstructed and no fluid is flowing in the suction passage 12, the second chamber portion 46 will be at near atmospheric pressure such that the diaphragm 30 will be in a rest position in contact with the inlet port 50 whereby flow of anitcoagulant into the first chamber portion 44 is prevented. In addition, anticoagulant located within the supply tube 60 is held against flowing out of the tube 60 such that the tube 60 remains in a primed condition.

When a fluid such as blood is aspirated into the device through the holes 70, the pressure within the suction passage 12 decreases such that a vacuum is supplied to the fluid connection 66 to create a sub-atmospheric pressure within the second chamber portion 46, resulting in the diaghragm being repositioned out of contact with the inlet port 50. Consequently, anticoagulant flows into the cavity formed by the mixing cap 68 where it is mixed with blood entering the suction passage 12 and flows with the blood through the suction tube 11 and out of the main body portion 10.

It should be noted that the diameter of the supply tube 60 is selected relative to the diameter of the suction tube 11 such that a precise predetermined amount of anticoagulant will be supplied and mixed with a predetermined volume of blood being aspirated into the passage 12.

It should also be noted that the present invention may be formed as a disposable device and the elements of the device, with the exception of the flexible diaphragm, are preferably produced from a molded plastic material.

Therefore, it should be apparent that the present device provides means for accurately initiating and terminating the flow of anticoagulant to be mixed with blood in response to the flow of blood through the suction passage. In addition, it should be apparent that the present device provides an accurate means for metering the amount of anticoagulant provided for mixing with the blood removed by the device as well as provides an easily operated device which is automatically actuated in response to the aspiration of fluids.

While the form of apparatus herein described constitutes a preferred embodiment of the invention, it is to be understood that the invention is not limited to this precise form of apparatus and that changes may be made therein without departing from the scope of the invention which is defined in the appended claims.

What is claimed is:

1. A suction metering and mixing device comprising:
    means defining a suction passage for sucking a first fluid into said device;
    means defining a chamber in fluid communication with said suction passage;
    supply means for supplying a second fluid to said chamber;
    an inlet port formed in said chamber defining a passage for entry of said second fluid into said chamber;
    an outlet port formed in said chamber defining a passage for allowing said second fluid to exit from said chamber;
    a diaphragm dividing said chamber into first and second portions wherein said inlet port is in fluid communication with said first portion, said diaphragm being located in a rest position in contact with said inlet port whereby flow of said second fluid into said first chamber portion is prevented;
    a fluid passage extending from said first chamber portion and connected for fluid communication with said suction passage such that said second fluid flows out of said first chamber portion through said outlet port and into said fluid passage during passage of said second fluid from said first chamber portion to said suction passage; and
    means for causing said diaphragm to be repositioned to permit said second fluid to flow to said suction passage via said first chamber portion.

2. The device of claim 1 wherein said diaphragm moves from said position in contact with said inlet port in response to the presence of said first fluid in said suction passage.

3. The device of claim 1 wherein said means for causing said diaphragm to be repositioned includes means for supplying a vacuum to said second chamber portion.

4. The device of claim 3 wherein said means for supplying a vacuum to said second chamber portion includes a fluid connection between said second chamber portion and said suction passage.

5. The device of claim 1 wherein said suction passage includes an inlet opening for receiving said first fluid and said second fluid enters said suction passage through said inlet opening.

6. The device of claim 5 wherein said suction passage inlet opening is located at a first end of said suction passage and a second opposite end of said passage is adapted to be connected to a vacuum source.

7. The device of claim 6 wherein said means for causing said diaphragm to be repositioned includes a fluid connection between said second chamber portion and said suction passage whereby a vacuum is supplied to said second chamber portion.

8. The device of claim 7 wherein said fluid connection is located intermediate said first and second ends of said suction passage.

9. A suction metering and mixing device comprising:
    means defining a suction passage for sucking a first fluid into said device;
    means defining a chamber in fluid communication with said suction passage;
    supply means for supplying a second fluid to said chamber;
    an inlet port formed in said chamber defining a passage for entry of said second fluid into said chamber,
    an outlet port formed in said chamber defining a passage for allowing said second fluid to exit from said chamber;
    a diaphragm dividing said chamber into first and second portions wherein said inlet port is in fluid communication with said first portion, said diaphragm being located in a rest position to prevent flow of said second fluid from said supply means into said first chamber;
    a fluid passage extending from said first chamber portion and connected for fluid communication with said suction passage such that said second fluid flows out of said first chamber portion through said outlet port and into said fluid passage during passage of said second fluid from said first chamber portion to said suction passage; and means for supplying vacuum to said second chamber portion whereby said diaphragm is caused to be repositioned to permit said second fluid to flow into said suction passage via said first chamber portion.

10. The device of claim 9 wherein said diaphragm is positioned in contact with said inlet port in said rest position whereby flow of said second fluid into said chamber is prevented.

11. The device of claim 9 wherein said means for supplying vacuum to said second chamber portion causes a vacuum to be supplied to said second chamber portion in response to the presence of said first fluid in said suction passage.

12. The device of claim 9 wherein said means for supplying vacuum includes a fluid connection between said second chamber portion and said suction passage.

13. The device of claim 9 wherein said suction passage includes an inlet opening for receiving said fluid and said second fluid enters said suction passage through said inlet opening.

14. The device of claim 13 wherein said suction passage inlet opening is located at a first end of said suction passage and a second opposite end of said suction passage is adapted to be connected to a vacuum source.

15. The device of claim 14 wherein said means for supplying vacuum to said second chamber portion includes a fluid connection between said second chamber portion and said suction passage.

16. The device of claim 15 wherein said fluid connection is located intermediate said first and second ends of said suction passage.

17. A suction metering and mixing device comprising:

an elongated suction tube having a first open end for receiving a mixture of blood and anticoagulant and a second end for connection to a vacuum source, said suction tube defining a first inner diameter;

an elongated supply tube extending parallel to said suction tube and having a first open end adjacent to said first end of said suction tube for supplying anticoagulant to said suction tube, said supply tube being attached along the length thereof to said suction tube and defining a second diameter smaller than said first diameter;

a suction chamber including a substantially circular base wall attached to said suction tube, a substantially circular chamber wall extending from said base wall and said suction tube and defining an inner and outer surface, a shoulder formed in said outer surface, a cap portion including a substantially circular top portion, a substantially circular cap wall extending from said top portion, a substantially circular flexible diaphragm member having a substantially planar surface and a flange portion extending around an outer edge thereof, said diaphragm extending across an outer edge of said chamber wall such that said flange portion is seated on said shoulder, said cap having a shoulder portion spaced from said top portion and contacting the outer peripheral edge of said diaphragm to retain said flange on said shoulder of said outer wall with said cap wall surrounding said chamber wall, said diaphragm separating said suction chamber into a fluid supply portion and a vacuum portion;

an inlet tube located substantially centrally in said cap portion and defining an inlet port at an end thereof, said inlet tube extending from said top portion toward said base portion to contact and flex said diaphragm such that said planar surface of said diaphragm forms a fluid seal over said inlet tube end, said inlet tube including a feed portion extending along said top portion of said cap toward said second end of said suction tube substantially parallel to said suction tube and having an inlet for connection to a source of anticoagulant;

a fluid connection extending from said suction tube to said vacuum portion of said suction chamber whereby vacuum applied to said second end of said suction tube may decrease the pressure in said vacuum portion of said chamber to draw said planar surface of said diaphragm toward said base portion of said chamber;

a supply passage formed integrally with said cap portion adjacent to said top portion;

a second end of said supply tube located adjacent to said suction chamber and being in fluid connection with said supply passage whereby fluid entering said fluid supply portion of said chamber may pass into said supply tube;

a tip portion attached adjacent to said first ends of said suction and supply tubes to define a fluid path between said suction and supply tubes, said tip portion having means defining holes therein whereby blood located exterior to said tip may be drawn through said tip and into said suction tube; and wherein entry of blood into said tip portion causes a vacuum to be created in said vacuum portion of said chamber such that said diaphragm is drawn away from said inlet tube to permit anticoagulant to flow into said fluid portion of said chamber and said supply tube whereby anticoagulant is mixed with blood in the fluid path defined by said tip portion.

* * * * *